US009072669B2

(12) United States Patent
Chen et al.

(10) Patent No.: US 9,072,669 B2
(45) Date of Patent: Jul. 7, 2015

(54) PLEUROTUS TUBER-REGIUM POLYSACCHARIDE FUNCTIONALIZED NANO-SELENIUM HYDROSOL WITH ANTI-TUMOR ACTIVITY AND PREPARATION METHOD THEREOF

(75) Inventors: Tianfeng Chen, Guangzhou (CN); Ka Hing Wong, Kowloon (HK); Hua-Lian Wu, Guangzhou (CN); Wenjie Zheng, Guangzhou (CN); Man Kin Wong, Kowloon (HK); Wing Yin Cornelia Man, Kowloon (HK)

(73) Assignee: THE HONG KONG POLYTECHNIC UNIVERSITY, Kowloon (HK)

( * ) Notice: Subject to any disclaimer, the term of this patent is extended or adjusted under 35 U.S.C. 154(b) by 125 days.

(21) Appl. No.: 13/557,864

(22) Filed: Jul. 25, 2012

(65) Prior Publication Data

US 2013/0029931 A1 Jan. 31, 2013

(30) Foreign Application Priority Data

Jul. 25, 2011 (CN) .......................... 2011 1 0208539

(51) Int. Cl.
*A61K 33/04* (2006.01)
*A61K 31/715* (2006.01)
*A61K 9/10* (2006.01)
*A61K 31/375* (2006.01)
*A61K 9/14* (2006.01)
*A61K 9/00* (2006.01)

(52) U.S. Cl.
CPC .................. *A61K 9/10* (2013.01); *A61K 31/375* (2013.01); *A61K 31/715* (2013.01); *A61K 33/04* (2013.01); *A61K 9/0095* (2013.01); *A61K 9/14* (2013.01)

(58) Field of Classification Search
CPC ... A61K 31/095; A61K 33/04; A61K 31/715; A61K 9/10
See application file for complete search history.

(56) References Cited

FOREIGN PATENT DOCUMENTS

| CN | 1184776 | A |   | 6/1998 |   |   |
|---|---|---|---|---|---|---|
| CN | 1415241 | A |   | 5/2003 |   |   |
| CN | 1415309 | A |   | 5/2003 |   |   |
| CN | 1415310 | A |   | 5/2003 |   |   |
| CN | 1789113 | A |   | 6/2006 |   |   |
| CN | 1947723 | A |   | 4/2007 |   |   |
| CN | 100998603 | A |   | 7/2007 |   |   |
| CN | 101040869 | A |   | 9/2007 |   |   |
| CN | 102895258 | A | * | 1/2013 | ........... | A61K 31/715 |

OTHER PUBLICATIONS

Zhang et al., Mater. Lett., 2004, 58, p. 2590-2594.*
Malinowska et al., Enzyme Microb. Technol., 2009, 44, p. 334-343.*
Zheng et al., "Formation and Stabilization of Selenium Nano-particles in Aqueous Solution of Undaria Pinnatifida Charv. Suringer Polysaccharide", Chemical Journal of Chinese Universities, Feb. 2007, vol. 28, No. 2, pp. 208-211.
Zhang et al., "Creation of Highly Stable Selenium Nanoparticles Capped with Hyperbranched Polysaccharide in Water", Langmuir, Oct. 2010 vol. 26, No. 22, pp. 17617-17623.

* cited by examiner

*Primary Examiner* — Jonathan S Lau
(74) *Attorney, Agent, or Firm* — Buchanan Ingersoll & Rooney PC (57) ABSTRACT

The preparation of *Pleurotus tuber-regium* polysaccharide functionalized nano-selenium hydrosol with anti-tumor activity includes the following steps: 1) at normal temperature and under normal pressure, adding a Vitamin C solution to an aqueous solution of *Pleurotus tuber-regium* polysaccharides, and mixing uniformly; 2) adding dropwise a selenium dioxide solution or a selenite solution to the solution while mixing uniformly; and 3) adding water to the solution to a pre-determined volume, to obtain a *Pleurotus tuber-regium* polysaccharide functionalized nano-selenium hydrosol when the red color of the product is no longer deepened. The polysaccharides are used to control the particle size of nano-selenium, to obtain functionalized nano-elemental selenium with high anti-tumor activity and low toxicity. The anti-tumor activity of the biologically active molecule polysaccharides and the physiological effect of nano-selenium are combined, and a synergistic anti-tumor effect is achieved.

13 Claims, 5 Drawing Sheets

PLEUROTUS TUBER-REGIUM POLYSACCHARIDE FUNCTIONALIZED NANO-SELENIUM HYDROSOL WITH ANTI-TUMOR ACTIVITY AND PREPARATION METHOD THEREOF

TECHNICAL FIELD

The present invention relates to the rapid preparation of functionalized nano-selenium, and more particularly, to a *Pleurotus tuber-regium* polysaccharide functionalized nano-selenium hydrosol with anti-tumor activity and a preparation method thereof.

BACKGROUND ART

Selenium is one of the 15 kinds of essential trace elements, and exerts an anti-tumor activity, an antioxidation activity, an anti-aging activity, an immune enhancing activity, a protection and restoration effect on cells, an antagonistic effect to reduce harmful heavy metals and other important biological activities in vivo. Occurrence and development of up to 40 types of diseases, including AIDS, liver cancer, Keshan disease, Kashin-Beck disease, and cardiovascular and cerebrovascular diseases, is closely associated with selenium deficiency.

For those with a low level of selenium or selenium deficiency, supplementation of an appropriate amount of selenium can enhance immunity, maintain the normal functions of vital organs such as heart, liver, lung and stomach, and prevent the occurrence of tumors, liver diseases and cardiovascular and cerebrovascular diseases. More than 40 countries belong to selenium deficient areas globally, and several provinces in China are part of selenium deficient zones or low-level selenium zones, and the incidence of tumors, liver diseases and cardiovascular and cerebrovascular diseases are high in these areas and zones, so people in these areas and zones need to be supplemented with selenium.

However, as a nutritional supplement or a cancer preventing agent, the range between a beneficial dose and a toxic dose of selenium is very narrow, such that selenium poisoning occurs easily, which severely limits the potential application of selenium in the prevention and treatment of diseases, especially in the prevention and treatment of cancers. The toxicity of selenium depends on the chemical form thereof, and the current study results find that the toxicity of inorganic selenium compounds is stronger than that of organic selenium compounds, the toxicity of selenocysteine is similar to that of sodium selenite, and the toxicity of sodium selenite is stronger than that of nano-selenium. Nano-selenium has the advantages of high bioavailability, high biological activity and low toxicity.

Nano-elemental selenium is usually prepared by a reduction method where an oxysalt or oxide of selenium is reduced by various reducing agents to obtain the elemental selenium, and at the same time, the morphology is modified or regulated by using a modifier or a regulating agent in order to obtain a product with desired particle size and morphology.

Endeavours in the field include that by Zhang Jinsong et al., (Chinese Patent application publication no. CN1184776A), in which was disclosed the use of a reducing agent in protein or peptide solution system to reduce the protein or peptide controlled nano-selenium selenium compounds, whereby solid nano elemental selenium is obtained following separation and drying.

Other patent literature include Chinese patent application publication no. CN1415241A "Glucomannan nano-selenium and the preparation method thereof", Chinese patent application publication no. CN415309 A "Melatonin nano-selenium and the preparation method thereof", Chinese patent application publication no. CN1415310 A "Chitin nano-selenium and the preparation method thereof", Chinese patent application publication no. CN1415308 A, "Amino acid nano-selenium and the preparation method thereof" and Chinese patent application publication no CN1789113 A), "A method for preparing nano-selenium sol."

Other endeavours include Chinese patent application publication no. CN1947723 A "A liquid polysaccharide nano-selenium and the preparation and storage thereof"; Chinese patent application publication no. CN100998603 A "Liquid vitamin C complex nano elemental selenium and the preparation and preservation methods thereof" and Chinese patent application publication no CN101040869 A "Liquid amino acid coupled elemental nano-selenium and the preparation and preservation methods thereof patent." Within the scientific literature those by Huang Liang et al. (Chemical Journal of Chinese Universities [J], 2007, 28 (2): 208 to 211) which discloses polysaccharides of *Undaria pinnatifida* or an oxidative degraded product thereof as effective in modifying and stabilizing nano-selenium; and by Zhang et al (Langmuir [J], 2010, 26 (22): 17 617 to 17623) which discloses that the many of the multi-branched polysaccharides display good control effect on the morphology and particle size of nano elemental selenium.

SUMMARY

The technical problem to be solved in the present invention is to provide a *Pleurotus tuber-regium* polysaccharide functionalized nano-selenium hydrosol with anti-tumor activity and a preparation method thereof, so as to overcome the disadvantage of the preparation method of nano-elemental selenium in the prior art in which the use of a modifer or a regulating agent cannot effectively improve the biological activities of nano-elemental selenium in a first aspect, the present invention comprises a *Pleurotus tuber-regium* polysaccharide functionalized nano-selenium hydrosol with anti-tumor activity, comprising:

*Pleurotus tuber-regium* polysaccharides, in a concentration range of 10 mg·$L^{-1}$-1000 mg·$L^{-1}$;

Vitamin C, in a concentration range of 0.02 mmol·$L^{-1}$-20 mmol·$L^{-1}$; and nano-selenium, in a concentration range of 0.005 mmol·$L^{-1}$-5 mmol·$L^{-1}$. In a second aspect, the present invention provides *Pleurotus tuber-regium* polysaccharide functionalized nano-selenium hydrosol with anti-tumor activity, comprising

*Pleurotus tuber-regium* polysaccharides, in a concentration range of 10 mg·$L^{-1}$-800 mg·$L^{-1}$;

Vitamin C, in a concentration range of 2 μmol·$L^{-1}$-0.01 mmol·$L^{-1}$; and nano-selenium, in a concentration range of 0.1 mmol·$L^{-1}$-5 mmol·$L^{-1}$.

In a third aspect, the present invention provides a method for preparing the *Pleurotus tuber-regium* polysaccharide functionalized nano-selenium hydrosol with anti-tumor activity, including the following steps:

Step 1) at normal temperature and under normal pressure, adding a vitamin C solution to an aqueous solution of *Pleurotus tuber-regium* polysaccharide, and mixing uniformly;

Step 2) adding dropwise a selenium dioxide solution or a selenite solution to the solution obtained in Step 1 while mixing uniformly; and Step 3) adding water to the solution obtained in Step 2 to a pre-determined volume, to obtain a *Pleurotus tuber-regium* polysaccharide functionalized nano-selenium hydrosol when the red color of the product is no longer deepened.

In the *Pleurotus tuber-regium* polysaccharide functionalized nano-selenium hydrosol with anti-tumor activity according to an embodiment of the third aspect of the present invention, the concentration of the aqueous solution of *Pleurotus tuber-regium* polysaccharide is 30 mg·L$^{-1}$-3000 mg·L$^{-1}$, the concentration of the Vitamin C solution is 0.2 mmol·L$^{-1}$-200 mmol·L$^{-1}$, and the concentration of the selenium dioxide solution or the sodium selenite solution is 0.05 mmol·L$^{-1}$-50 mmol·L$^{-1}$.

In the *Pleurotus tuber-regium* polysaccharide functionalized nano-selenium hydrosol with anti-tumor activity according to an alternative embodiment of the third aspect of the present invention, the concentration of the aqueous solution of *Pleurotus tuber-regium* polysaccharide is 100 mg·L$^{-1}$-3000 mg·L$^{-1}$, the concentration of the Vitamin C solution is 0.02 mol·L$^{-1}$-0.2 mol·L$^{-1}$, and the concentration of the selenium dioxide solution or the sodium selenite solution is $1\times10^{-6}$ mol·L$^{-1}$-$1\times10^{-2}$ mmol·L$^{-1}$.

In the *Pleurotus tuber-regium* polysaccharide functionalized nano-selenium hydrosol with anti-tumor activity according to a preferred embodiment of the present invention, the Vitamin C is a reductive Vitamin C.

In the *Pleurotus tuber-regium* polysaccharide functionalized nano-selenium hydrosol with anti-tumor activity according to a preferred embodiment of the present invention, the selenite is sodium selenite.

In the *Pleurotus tuber-regium* polysaccharide functionalized nano-selenium hydrosol with anti-tumor activity according to a preferred embodiment of the present invention, *Pleurotus tuber-regium* polysaccharides are water-soluble *Pleurotus tuber-regium* polysaccharides, chemically modified hot alkali-soluble *Pleurotus tuber-regium* polysaccharides, or a combination thereof.

The present invention further provides a use of the *Pleurotus tuber-regium* polysaccharide functionalized nano-selenium hydrosol with anti-tumor activity, where the *Pleurotus tuber-regium* polysaccharide functionalized nano-selenium in the *Pleurotus tuber-regium* polysaccharide functionalized nano-selenium hydrosol is used in the preparation of anti-tumor drugs.

The present invention further provides a storage method of the *Pleurotus tuber-regium* polysaccharide functionalized nano-selenium hydrosol with anti-tumor activity, where the *Pleurotus tuber-regium* polysaccharide functionalized nano-selenium hydrosol is stored in the form of a sol at 2-10° C.

The *Pleurotus tuber-regium* polysaccharide functionalized nano-selenium hydrosol with anti-tumor activity, and the preparation method, the use and the storage method thereof for implementing the present invention have the following beneficial effects:

(1) In the present invention, edible and medicinal *Pleurotus tuber-regium* polysaccharides with antioxidation activity, anti-tumor activity, antiviral activity, anti-aging activity, immune enhancing activity and other biological activities are used as the molecule for functionalizing nano-selenium, so that the anti-tumor activity of the *Pleurotus tuber-regium* polysaccharide molecule and the physiological effect of nano-selenium are combined and a synergistic anti-tumor effect is achieved, thereby providing a preferred regimen in treatment of cancer with combined chemotherapy in clinic.

(2) The structure of *Pleurotus tuber-regium* polysaccharides used in the present invention has particular features. That is, the *Pleurotus tuber-regium* polysaccharide are aggregate polymers formed by multiple monosaccharide molecules connected through glycosidic bonds, having a polyhydroxy structure, good hydrophilicity, and also a hydrophobic segment, such that when being used to modify the surface of nano-selenium, the *Pleurotus tuber-regium* polysaccharides can achieve a good effect of controlling the particle size of nano-selenium and stabilizing nano-selenium, improving the water solubility of nano-selenium at the same time, thereby enhancing the affinity of selenium to cancer cells and increasing the intake of nano-selenium of tumor cells, so as to achieve the treatment effect with reduced dose, improved efficacy, and reduced toxic side effects.

(3) In the reaction system for preparing nano-selenium according to the present invention, only Vitamin C is used as the reducing agent, and the *Pleurotus tuber-regium* polysaccharides are used as regulation molecules for functionalizing nano-selenium, without adding any other templates, thereby avoiding possible adverse effects in practical application.

(4) In the product *Pleurotus tuber-regium* polysaccharide functionalized nano-selenium hydrosol with anti-tumor activity obtained in the present invention, the concentration of nano-selenium may be adjusted according to the needs in application, and the concentrations of *Pleurotus tuber-regium* polysaccharides and the reducing agent Vitamin C may also be appropriately changed, where the operation is simple, quick and easy.

BRIEF DESCRIPTION OF THE DRAWINGS

The present invention will become more fully understood from the detailed description given herein below for illustration only, and thus are not limitative of the present invention, and wherein.

*regium* polysaccharides is 300.0 mg·L$^{-1}$, the concentration of selenium is 1.0 mmol·L$^{-1}$, and the concentration of Vitamin C is 4.0 mmol·L$^{-1}$.

DETAILED DESCRIPTION

*Pleurotus tuber-regium* is a valuable, edible and medicinal fungi in tropical regions, and the sclerotium can be used to effectively treat various diseases such as gastric disease, asthma, hypertension, mastitis, diabetes, coronary heart diseases and tumor. It is able to promote fetal development and improve the survival rate of preterm children and have an immune function enhancing effect, an anti-tumor effect, a virus inhibiting effect, and other physiological functions. Polysaccharides are the main active ingredients of *Pleurotus tuber-regium*. It is found in the current study that *Pleurotus tuber-regium* polysaccharides is able to enhance the immune function and has strong tumor and virus inhibiting effect.

Therefore, *Pleurotus tuber-regium* polysaccharides are used in the present invention to functionalize nano-selenium. That is, *Pleurotus tuber-regium* polysaccharides with antioxidation activity, anti-tumor activity, antivirus activity, anti-aging activity, immune enhancing activity and other activities are introduced into a liquid-phase nano-selenium system, in order to improve the bioavailability and biological activity, reduce the cytotoxicity and obtain nano-selenium with significant anti-tumor activity, where the anti-tumor activity of *Pleurotus tuber-regium* polysaccharides is enhanced by means of synergetic effect. As a result, a *Pleurotus tuber-regium* polysaccharide functionalized nano-selenium hydrosol with anti-tumor activity is provided.

The *Pleurotus tuber-regium* polysaccharide functionalized nano-selenium hydrosol with anti-tumor activity according to the present invention contains: *Pleurotus tuber-regium* polysaccharides, in a concentration range of 10 mg·L$^{-1}$-1000 mg·L$^{-1}$; Vitamin C, in a concentration range of 0.02 mmol·L$^{-1}$-20 mmol·L$^{-1}$; and nano-selenium in a concentration range of 0.005 mmol·L$^{-1}$-5 mmol·L$^{-1}$.

Alternatively, the *Pleurotus tuber-regium* polysaccharide functionalized nano-selenium hydrosol with anti-tumor activity according to the present invention may contain: *Pleurotus tuber-regium* polysaccharides, in a concentration range of 10 mg·L$^{-1}$-800 mg·L$^{-1}$; Vitamin C, in a concentration range of 2 μmol·L$^{-1}$-0.01 mmol·L$^{-1}$; and nano-selenium, in a concentration range of 0.1 mmol·L$^{-1}$-5 mmol·L$^{-1}$. The *Pleurotus tuber-regium* polysaccharide functionalized nano-selenium hydrosol with anti-tumor activity according to the present invention is prepared by the method below.

First, at normal temperature and under normal pressure, a Vitamin C solution is added to an aqueous solution of *Pleurotus tuber-regium* polysaccharides, and mixed uniformly. The Vitamin C is preferably a reductive Vitamin C.

Next, a selenium dioxide solution or a selenite solution is added to the solution obtained above, while mixing uniformly, where the selenite may be sodium selenite.

Finally, water is added to the solution obtained above to a pre-determined volume, so as to obtain a *Pleurotus tuber-regium* polysaccharide functionalized nano-selenium hydrosol when the red color of the product is no longer deepened.

In the preparation process, the concentration of the aqueous solution of *Pleurotus tuber-regium* polysaccharides is 30 mg·L$^{-1}$-3000 mg·L$^{-1}$, the concentration of the Vitamin C solution is 0.2 mmol·L$^{-1}$-200 mmol·L$^{-1}$, and the concentration of the selenium dioxide or the sodium selenite solution is 0.05 mmol·L$^{-1}$-50 mmol·L$^{-1}$.

Alternatively, the concentration of the aqueous solution of *Pleurotus tuber-regium* polysaccharide may be 100 mg·L$^{-1}$-3000 mg·L$^{-1}$, the concentration of the Vitamin C solution may be 0.02 mol·L$^{-1}$-0.2 mol·L$^{-1}$, and the concentration of the selenium dioxide solution or the sodium selenite solution may be $1\times10^{-6}$ mol·L$^{-1}$-$1\times10^{-2}$ mmol·L$^{-1}$.

Based on the amount of the *Pleurotus tuber-regium* polysaccharide functionalized nano-selenium hydrosol required for different concentrations, the volumes of the raw materials of the concentrations may be calculated. In the following embodiments, the specific concentrations and volumes of the raw materials for preparing different concentrations of products are described.

The *Pleurotus tuber-regium* polysaccharide functionalized nano-selenium hydrosol with anti-tumor activity prepared in the present invention may be used to prepare anti-tumor drugs. The *Pleurotus tuber-regium* polysaccharide functionalized nano-selenium hydrosol may be stored in the form of sol at 2-10° C.

Herein, *Pleurotus tuber-regium* may be one or more selected from artificially cultivated *Pleurotus tuber-regium* species and wild *Pleurotus tuber-regium* species; and may also be one or more selected from *Pleurotus tuber-regium* species having some differences in phylogenesis in different regions, for example, from *Pleurotus tuber-regium* species in Yunnan and Fujian, China, and *Pleurotus tuber-regium* species in foreign countries such as Nigeria, Malaysia, Papua, New Guinea, and New Caledonia.

In the implementation, *Pleurotus tuber-regium* polysaccharides are water-soluble *Pleurotus tuber-regium* polysaccharides, chemically modified hot alkali-soluble *Pleurotus tuber-regium* polysaccharides, or a combination thereof.

The water-soluble *Pleurotus tuber-regium* polysaccharide refers to water-soluble polysaccharides from mycelium of *Pleurotus tuber-regium* and water-soluble polysaccharides from sclerotium of *Pleurotus tuber-regium*, for example, mp-1 having a molecular weight $M_w$ of 17.03 kDa and a main chain structure of $[\beta\text{-Glc}(1\text{-}6)\text{-Fru}]_n\text{-}[\alpha\text{-Gla}(1\text{-}6)\text{-}\beta\text{-Rha}(1\text{-}3)\text{-}\beta\text{-Man}(1\text{-}4)]_m$, mp-2 having a molecular weight of 13.79 kDa and a main chain structure of $[\beta\text{-Glc}(1\text{-}6)\text{-Fru}]_n\text{-}[\alpha\text{-Rha}(1\text{-}6)]_m$, sp-1 having a molecular weight of 16.96 kDa and a main chain structure of $[\beta\text{-Glc}(1\text{-}6)\text{-Fru}]_n\text{-}[\alpha\text{-Glc}(1\text{-}6)]_m$, sp-2 having a molecular weight of 131.96 kDa and a main chain structure being β-catenin containing β-Gla, and sp-3 having a molecular weight of 174.40 kDa and a main chain structure of $\beta\text{- -Glc }(1\text{-}6)\text{ -Fru}]_n$.

The hot alkali-soluble *Pleurotus tuber-regium* polysaccharide refer to a hot alkali-soluble polysaccharides from mycelium of *Pleurotus tuber-regium* and a hot alkali-soluble polysaccharides from sclerotium of *Pleurotus tuber-regium*, and is a homopolysaccharide having a main chain of β-(1-3)-D-glucan, with one branched glucose residue bonded through β-(1-6) every three glucose residues, so that different products are obtained after chemical modification, for example, sulfated *Pleurotus tuber-regium* polysaccharides and carboxymethylated *Pleurotus tuber-regium* polysaccharides.

The present invention is further described in detail below with reference to the following examples and accompanying drawings, but the implementation of the present invention is not limited thereto.

Example 1

At normal temperature and under normal pressure (15-35° C., 1 standard atmospheric pressure), 0, 0.25, 0.5, 1.0, 2.0, 3.0, 4.0, 5.0 and 6.0 ml of a water-soluble *Pleurotus tuber-regium* polysaccharide solution having a mass concentration of 2.5 g·L$^{-1}$ were respectively added into nine 25-ml volumetric flasks containing 10 ml of double distilled water; 1.0 ml of a Vitamin C solution having a concentration of 0.1 mol·L$^{-1}$ was added, and gently shaken to obtained a well-mixed solution; and then 1.0 ml of a sodium selenite solution having a concentration of 0.025 mol·L$^{-1}$ was added dropwise, and gently shaken while adding to mix uniformly; and after the addition, water was added to a pre-determined volume of 25 ml, so as to obtain products when the red color was no longer deepened, where the concentrations of the water-soluble *Pleurotus tuber-regium* polysaccharide were respectively 0, 25, 50, 100, 200, 300, 400, 500 and 600 mg·L$^{-1}$, the concentration of nano-selenium was 1.0 mmol·L$^{-1}$, and the concentration of Vitamin C was 4.0 mmol·L$^{-1}$.

Figure 1:
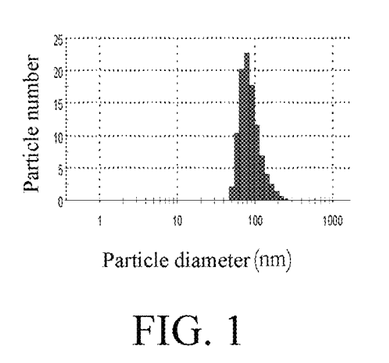
FIG. 1 is a laser light scattering image of *Pleurotus tuber-regium* polysaccharide functionalized nano-selenium in a hydrosol, where the concentration of water-soluble *Pleurotus tuber-regium* polysaccharides is 100.0 mg·L$^{-1}$, the concentration of selenium is 1.0 mmol·L$^{-1}$, and the concentration of Vitamin C is 4.0 mmol·L$^{-1}$.
Figure 2:
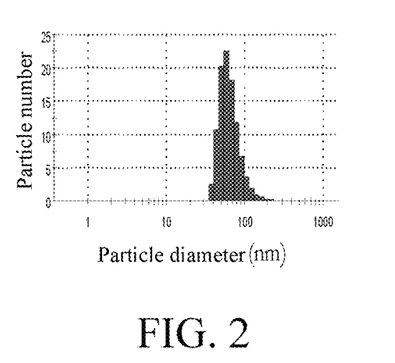
FIG. 2 is a laser light scattering image of *Pleurotus tuber-regium* polysaccharide functionalized nano-selenium in a hydrosol, where the concentration of water-soluble *Pleurotus tuber-regium* polysaccharides is 300.0 mg·L$^{-1}$, the concentration of selenium is 1.0 mmol·L$^{-1}$, and the concentration of vitamin C is 4.0 mmol·L$^{-1}$.

The products may be stored in the form of sol in an aqueous solution at 2-10° C. The nano particle size and the polydispersity index of the product were measured by using a Nano-ZS (Malvern Instruments Limited), and the particle size counting was indicated by number. Representative data of laser light scattering is shown in FIG. 1 and FIG. 2 (FIG. 1 is a laser light scattering image of *Pleurotus tuber-regium* polysaccharide functionalized nano-selenium in a hydrosol, where the concentration of water-soluble *Pleurotus tuber-regium* polysaccharides is 100.0 mg·L$^{-1}$; and FIG. 2 is a laser light scattering image of *Pleurotus tuber-regium* polysaccharide functionalized nano-selenium in a hydrosol, where the concentration of water-soluble *Pleurotus tuber-regium* polysaccharides is 300.0 mg·L$^{-1}$).

The results show that, under the regulation of *Pleurotus tuber-regium* polysaccharide, the particle size of functionalized nano-selenium is far less than that of the control group, indicating that *Pleurotus tuber-regium* polysaccharides have good regulation effect on the particle size of nano-selenium, and the particle size of the prepared product is about 100 nm.

Figure 3:
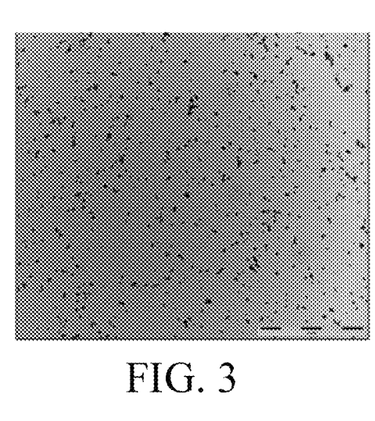
FIG. 3 is a TEM image of *Pleurotus tuber-regium* polysaccharide functionalized nano-selenium in a hydrosol, where the concentration of water-soluble *Pleurotus tuber-regium* polysaccharides is 100.0 mg·L$^{-1}$, the concentration of selenium is 1.0 mmol·L$^{-1}$, and the concentration of Vitamin C is 4.0 mmol·L$^{-1}$.

FIG. 3 is a morphology image of polysaccharide functionalized nano-selenium characterized by using a TECNAI-10 transmission electron microscopy (Philips). The result shows that functionalized nano-selenium regulated by using *Pleurotus tuber-regium* polysaccharides has good dispersibility, and the product is a spherical nano-selenium.

Figure 4:
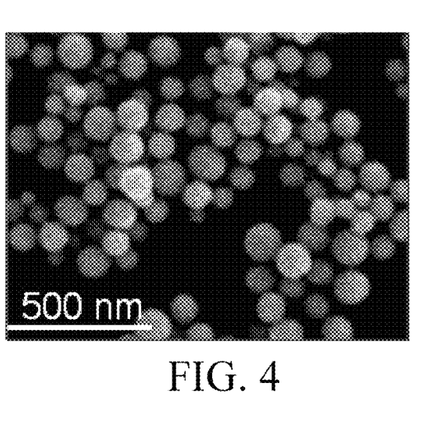
FIG. 4 is an SEM image of *Pleurotus tuber-regium* polysaccharide functionalized nano-selenium in a hydrosol, where the concentration of water-soluble *Pleurotus tuber-regium* polysaccharides is 300.0 mg·L$^{-1}$, the concentration of selenium is 1.0 mmol·L$^{-1}$, and the concentration of Vitamin C is 4.0 mmol·L$^{-1}$.

FIG. 4 is a scanning topography image of polysaccharide functionalized nano-selenium characterized by using an energy-dispersive X-ray analyzer (EX-250, Horiba), and the result also proves that functionalized nano-selenium is spherical and has a small particle size of about 100 nm.

Figure 5:
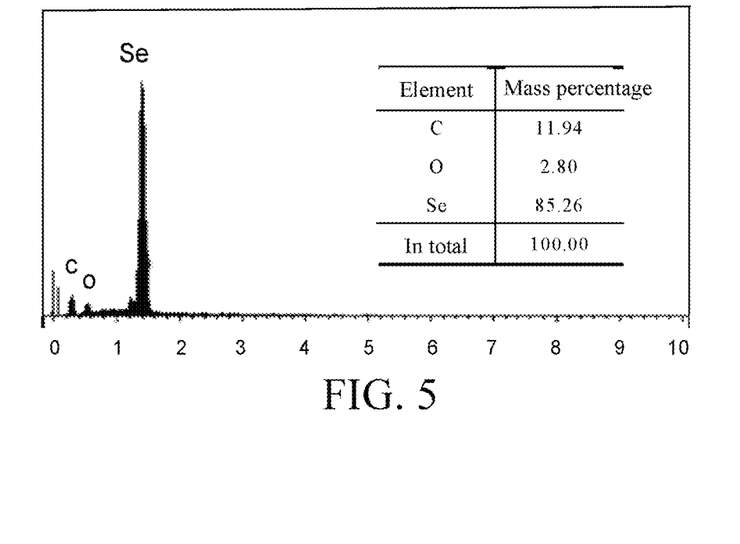
FIG. 5 is an EDX elemental analysis image of *Pleurotus tuber-regium* polysaccharide functionalized nano-selenium in a hydrosol, where the concentration of water-soluble *Pleurotus tuber-regium* polysaccharides is 300.0 mg·L$^{-1}$, the concentration of selenium is 1.0 mmol·L$^{-1}$, and the concentration of Vitamin C is 4.0 mmol·L$^{-1}$.

FIG. 5 is an elemental analysis image, and the result shows that the main element of functionalized nano-selenium is selenium, and C and O from polysaccharide also exist.

Figure 6:
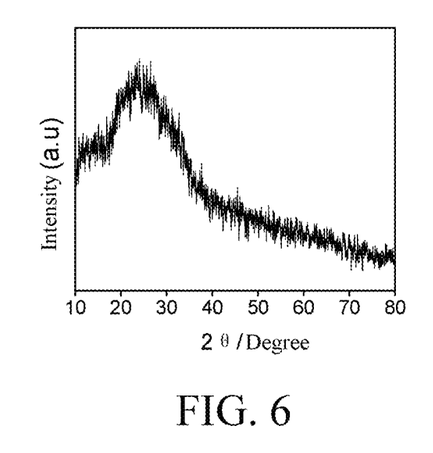
FIG. 6 is an XRD pattern of *Pleurotus tuber-regium* polysaccharide functionalized nano-selenium in a hydrosol, where the concentration of water-soluble *Pleurotus tuber-*

FIG. 6 shows a crystal form of water-soluble *Pleurotus tuber-regium* polysaccharide functionalized nano-selenium characterized by using an MSAL-XD2 X-ray diffractometer, and the result shows that functionalized nano-selenium is an amorphous selenium.

Figure 7:
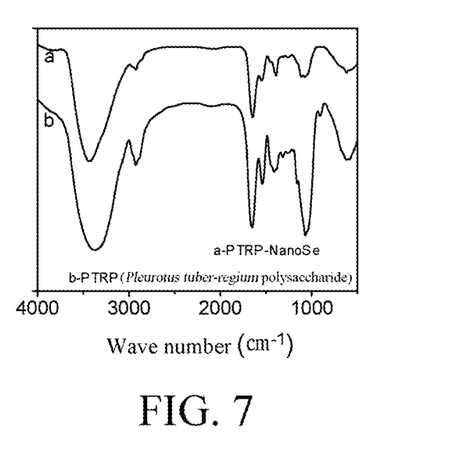
FIG. 7 is an FT-IR spectrum of *Pleurotus tuber-regium* polysaccharide functionalized nano-selenium in a hydrosol, where the concentration of water-soluble *Pleurotus tuber-regium* polysaccharides is 300.0 mg·L$^{-1}$, the concentration of selenium is 1.0 mmol·L$^{-1}$, and the concentration of Vitamin C is 4.0 mmol·L$^{-1}$.

FIG. 7 shows the interaction between water-soluble *Pleurotus tuber-regium* polysaccharides and elemental selenium characterized by using a Fourier transform infrared spectrometer, and the result shows that nano-selenium and *Pleurotus tuber-regium* polysaccharides interact with each other through physical adsorption.

Figure 8:
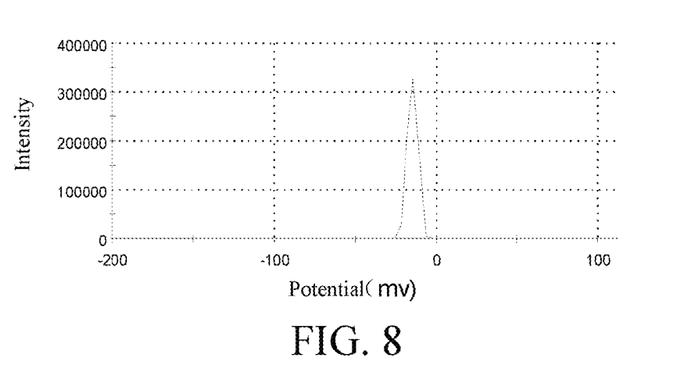
FIG. 8 is a Zeta potential diagram of *Pleurotus tuber-regium* polysaccharide functionalized nano-selenium in a hydrosol, where the concentration of water-soluble *Pleurotus tuber-regium* polysaccharides is 300.0 mg·L$^{-1}$, the concentration of selenium is 1.0 mmol·L$^{-1}$, and the concentration of Vitamin C is 4.0 mmol·L$^{-1}$.

FIG. 8 is a Zeta potential diagram of the water-soluble *Pleurotus tuber-regium* polysaccharide functionalized nano-selenium hydrosol characterized by using a Nano-ZS (Malvern Instruments Limited), where the absolute value of the potential is 8-9, indicating that the functionalized nano-selenium sol system is stable.

Figure 9:
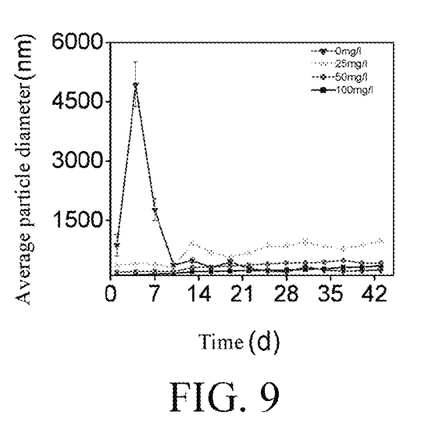
FIG. 9 is a stability tracking view of *Pleurotus tuber-regium* polysaccharide functionalized nano-selenium in a hydrosol, where the concentration of water-soluble *Pleurotus tuber-regium* polysaccharides is 0, 25, 50 and 100 mg·L$^{-1}$, the concentration of selenium is 1.0 mmol·L$^{-1}$, and the concentration of Vitamin C is 4.0 mmol·L$^{-1}$.
Figure 10:
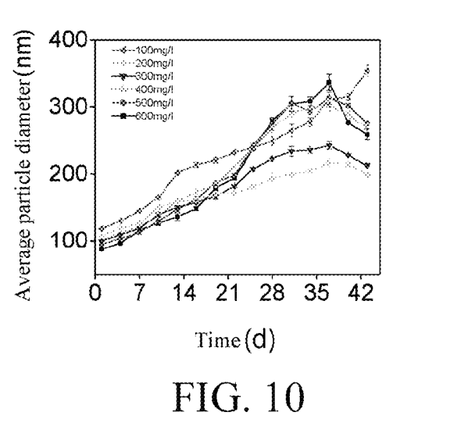
FIG. 10 is a stability tracking view of *Pleurotus tuber-regium* polysaccharide functionalized nano-selenium in a hydrosol, where the concentration of water-soluble *Pleurotus tuber-regium* polysaccharides is 100, 200, 300, 400, 500 and 600 mg·L$^{-1}$, the concentration of selenium is 1.0 mmol·L$^{-1}$, and the concentration of Vitamin C is 4.0 mmol·L$^{-1}$.

FIG. 9 and FIG. 10 show the stability of the water-soluble *Pleurotus tuber-regium* polysaccharide functionalized nano-selenium hydrosol over time characterized by using a Nano-ZS (Malvern Instruments Limited), the results show that within 3 weeks, the particle size range is maintained less than 200 nm, indicating that the stability of functionalized nano-selenium is high, and the change in the particle size in a certain period of time is not great.

The average particle size and PDI of the nano particles in the product are shown in Table 1, and the results show that the particle size of the functionalized nano-selenium is small, and with the increase of the concentration of polysaccharides, the particle size is reduced due to the concentration effect. The PDI values are less than 0.200, indicating that functionalized nano-selenium is well dispersed, and the particle size distribution is very narrow. In view of the test results, water-soluble polysaccharide has good regulation effect on the particle size of nano-selenium, and is a desired particle size regulating agent for nano-selenium.

TABLE 1

Average particle size and PDI of nano-selenium particles in Example 1

| | PTRP mg/L | | | | | | | | |
|---|---|---|---|---|---|---|---|---|---|
| | 0 | 25 | 50 | 100 | 200 | 300 | 400 | 500 | 600 |
| d · nm | 1167 | 168.8 | 141.7 | 118.3 | 107.8 | 100.3 | 100.3 | 93.22 | 86.23 |
| PdI | 0.682 | 0.144 | 0.118 | 0.090 | 0.158 | 0.147 | 0.168 | 0.173 | 0.150 |

(Note: PTRP is an abbreviation for water-soluble *Pleurotus tuber-regium* polysaccharide)

Example 2

At normal temperature and under normal pressure (15-35° C., 1 standard atmospheric pressure), 3.0 ml of a water-soluble *Pleurotus tuber-regium* polysaccharide solution having a mass concentration of 2.5 g·L$^{-1}$ was added to seven 25-ml volumetric flasks containing 10 ml of double distilled water; subsequently, 0, 0.125, 0.25, 0.5, 1.0, 1.5 and 2.0 ml of a Vitamin C solution having a concentration of 0.1 mol·L$^{-1}$ were added respectively, and gently shaken to obtain a well-mixed solution; after that, 0, 0.125, 0.25, 0.5, 1.0, 1.5 and 2.0 ml of a sodium selenite solution having a concentration of 0.025 mol·L$^{-1}$ were added dropwise to the corresponding volumetric flasks respectively, and gently shaken to mix uniformly; and after the addition, water was added to a pre-determined volume of 25 ml, such that when the red color was no longer deepened, the products are obtained, where the concentration of water-soluble *Pleurotus tuber-regium* polysaccharides was 300 mg·L$^{-1}$, and the concentrations of Se were respectively 0, 0.125, 0.25, 0.50, 1.0, 1.50 and 2.0 mmol·L$^{-1}$, and the corresponding concentrations of Vitamin C were respectively 0, 0.5, 1.0, 2.0, 4.0, 6.0 and 8.0 mmol·L$^{-1}$.

The nano particle size and the polydispersity index of the product were measured by using a Nano-ZS (Malvern Instruments Limited), and the particle size counting was indicated by number. The average particle size and PDI of nano particles in the product are shown in Table 2.

TABLE 2

Average particle size and PDI of nano-selenium particles in Example 2

| | Se(IV)mmol · L$^{-1}$ | | | | | | |
|---|---|---|---|---|---|---|---|
| | 0 | 0.125 | 0.25 | 0.50 | 1.0 | 1.5 | 2.0 |
| Vc mmol · L$^{-1}$ | 0 | 0.125 | 0.25 | 0.50 | 1.0 | 1.5 | 2.0 |
| d · nm | 83.935 | 128.275 | 93.465 | 89.11 | 104.4 | 167.9 | 247.275 |
| PdI | 0.48175 | 0.36575 | 0.277 | 0.2025 | 0.1125 | 0.1425 | 0.19725 |

Example 3

At normal temperature and under normal pressure (15-35° C., 1 standard atmospheric pressure), 0, 0.5, 1.0, 2.0 and 3.0 ml of a water-soluble *Pleurotus tuber-regium* polysaccharide solution having a mass concentration of 2.5 g·L$^{-1}$ were respectively added to five 25-ml volumetric flasks containing 10 ml of double distilled water; subsequently, 1.0 ml of a Vitamin C solution having a concentration of 0.1 mol·L$^{-1}$ was added, and gently shaken to obtain a well-mixed solution; then, 1.0 ml of a sodium selenite solution having a concentration of 0.025 mol·L$^{-1}$ was added dropwise, and gently shaken while adding to mix uniformly; and after the addition, water was added to a pre-determined volume of 25 ml, so as to obtain *Pleurotus tuber-regium* polysaccharide functionalized nano-selenium products when the red color was no longer deepened, where the concentration of Se was 1 mmol·L$^{-1}$, the concentration of Vitamin C was 4 mmol·L$^{-1}$, and the concentrations of water-soluble *Pleurotus tuber-regium* polysaccharides were respectively 0, 50, 100, 200 and 300 mg·L$^{-1}$. The products may be stored in the form of sol in an aqueous solution at 2-10° C.

Example 4

At normal temperature and under normal pressure (15-35° C., 1 standard atmospheric pressure), 0, 0.5, 2.0, 4.0 and 6.0 ml of a carboxymethylated hot alkali-soluble *Pleurotus tuber-regium* polysaccharide solution having a mass concentration of 2.5 g·L$^{-1}$ were added to five 25-ml volumetric flasks containing 10 ml of double distilled water; next, 1.0 ml of a Vitamin C solution having a concentration of 0.1 mol·L$^{-1}$ is added, and gently shaken to obtain a well-mixed solution; then, 1.0 ml of a sodium selenite solution having a concentration of 0.025 mol·L$^{-1}$ were added dropwise, and gently shaken while adding to mix uniformly; and after the addition, water was added to a pre-determined volume of 25 ml, so as to obtain *Pleurotus tuber-regium* polysaccharide functionalized nano-selenium products when the red color was no longer deepened, where the concentration of Se was 1 mmol·L$^{-1}$, the concentration of Vitamin C was 4 mmol·L$^{-1}$, and the concentrations of carboxymethylated hot alkali-soluble *Pleurotus tuber-regium* polysaccharides were respectively 0, 50, 200, 400 and 600 mg·L$^{-1}$. The products may be stored in the form of sol in an aqueous solution at 2-10° C.

Example 5

At normal temperature and under normal pressure (15-35° C., 1 standard atmospheric pressure), 0, 0.5, 2.0, 4.0 and 6.0 ml of a sulfated hot alkali-soluble *Pleurotus tuber-regium* polysaccharide solution having a mass concentration of 2.5 g L$^{-1}$ were respectively added to five 25-ml volumetric flasks containing 10 ml of double distilled water; next, 1.0 ml of a Vitamin C solution having a concentration of 0.1 mol·L$^{-1}$ was added, and gently shaken to obtain a well-mixed solution; then, 1.0 ml of a sodium selenite solution having a concentration of 0.025 mol·L$^{-1}$ was added dropwise, and gently shaken while adding to mix uniformly; and after the addition, water was added to a pre-determined volume of 25 ml, so as to obtain *Pleurotus tuber-regium* polysaccharide functionalized nano-selenium products when the red color was no longer deepened, where the concentration of Se was 1 mmol·L$^{-1}$, and the concentration of Vitamin C was 4 mmol·L$^{-1}$, the concentrations of sulfated hot alkali-soluble *Pleurotus tuber-regium* polysaccharides were respectively 0, 50, 200, 400 and 600 mg·L$^{-1}$. The products may be stored in the form of sol in an aqueous solution at 2-10° C.

Example 6

At normal temperature and under normal pressure (15-35° C., 1 standard atmospheric pressure), 3.0 ml of a water-soluble *Pleurotus tuber-regium* polysaccharide solution having a mass concentration of 2.5 g·L$^{-1}$ was added to a 25-ml volumetric flask containing 10 ml of double distilled water; next, 1.0 ml of a Vitamin C solution having a concentration of 0.1 mol·L$^{-1}$ was added, and gently shaken to obtain a well-mixed solution; then 1.0 ml of a sodium selenite solution having a concentration of 0.025 mol·L$^{-1}$ was added dropwise, and gently shaken while adding to mix uniformly; and after the addition, water was added to a pre-determined volume of 25 ml, so as to obtain products when the red color was no longer deepened, where the concentration of Se was 1 mmol·L$^{-1}$, the concentration of Vitamin C was 4 mmol·L$^{-1}$, and the concentration of water-soluble *Pleurotus tuber-regium* polysaccharides was 300 mg·L$^{-1}$.

The product was dialyzed for 24 h (cut-off molecular weight of 6000), and then the content of selenium in the nano-selenium hydrosol was determined by a nitrification-ICP method. The dialysis product after quantification was subjected to anti-tumor activity test.

Figure 11:
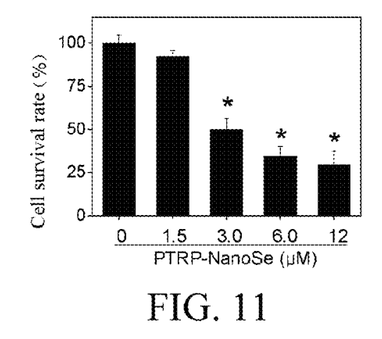
FIG. 11 shows cell survival rate detected by the MTT method when *Pleurotus tuber-regium* polysaccharide functionalized nano-selenium is used to inhibit growth of human breast cancer cell line MCF-7.

FIG. 11 shows results detected by MTT colorimetry (SpectroAmax™ 250) when water-soluble *Pleurotus tuber-regium* polysaccharide functionalized nano-selenium is used to inhibit growth of human breast cancer cell line MCF-7, and the results show that water-soluble *Pleurotus tuber-regium* polysaccharide functionalized nano-selenium can effectively inhibit the proliferative activity of human breast cancer cell line MCF-7, a dose-dependent response of the cell survival rate to the concentration of functionalized nano-selenium exists, and IC$_{50}$ is 3.0 µM.

Figure 12:
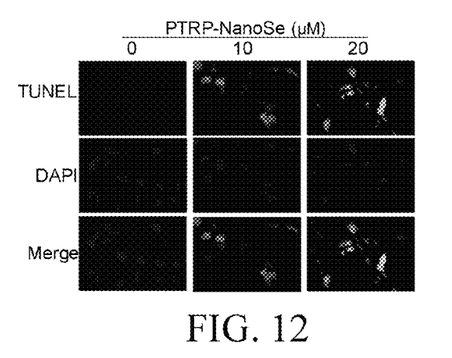
FIG. 12 shows DNA cleavage and chromatin condensation detected by the TUNEL method and the PADI method when *Pleurotus tuber-regium* polysaccharide functionalized nano-selenium is used to induce apoptosis of human breast cancer cell line MCF-7.

FIG. 12 shows DNA cleavage and chromatin condensation detected by the TUNEL method and the PADI method (Nikon Eclipse 80i fluorescence microscopy) when *Pleurotus tuber-regium* polysaccharide functionalized nano-selenium is used to induce apoptosis of human breast cancer cell line MCF-7, and the results show that water-soluble *Pleurotus tuber-regium* polysaccharide functionalized nano-selenium can induce DNA cleavage and chromatin condensation of the cell line MCF-7, and with the increase of the concentration of functionalized nano-selenium, DNA cleavage and chromatin condensation get serious.

Figure 13:
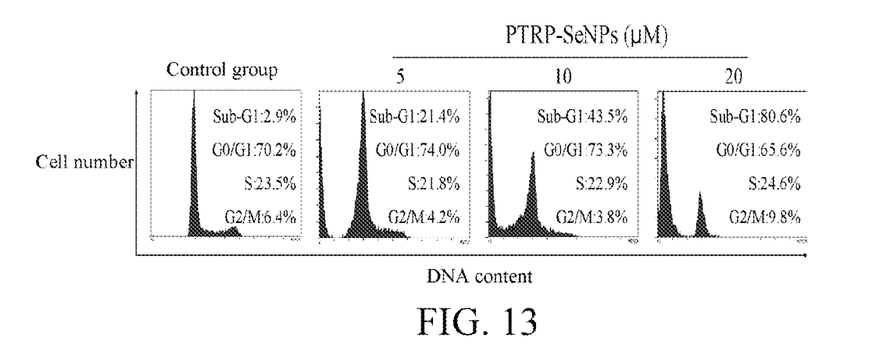
FIG. 13 shows cell apoptosis detected by flow cytometry when *Pleurotus tuber-regium* polysaccharide functionalized nano-selenium is used to induce apoptosis of human breast cancer cell line MCF-7.

FIG. 13 shows cell apoptosis detected by using an Epics XL-MCL flow cytometry (Beckman Coulter, Miami, Fla.) when *Pleurotus tuber-regium* polysaccharide functionalized nano-selenium is used to induce apoptosis of human breast cancer cell line MCF-7, and the results show that functionalized nano-selenium can induce apoptosis of the cell line MCF-7, and with the increase of the concentration of functionalized nano-selenium, the proportion of apoptotic cells is increased due to the dose-dependent response.

Figure 14:
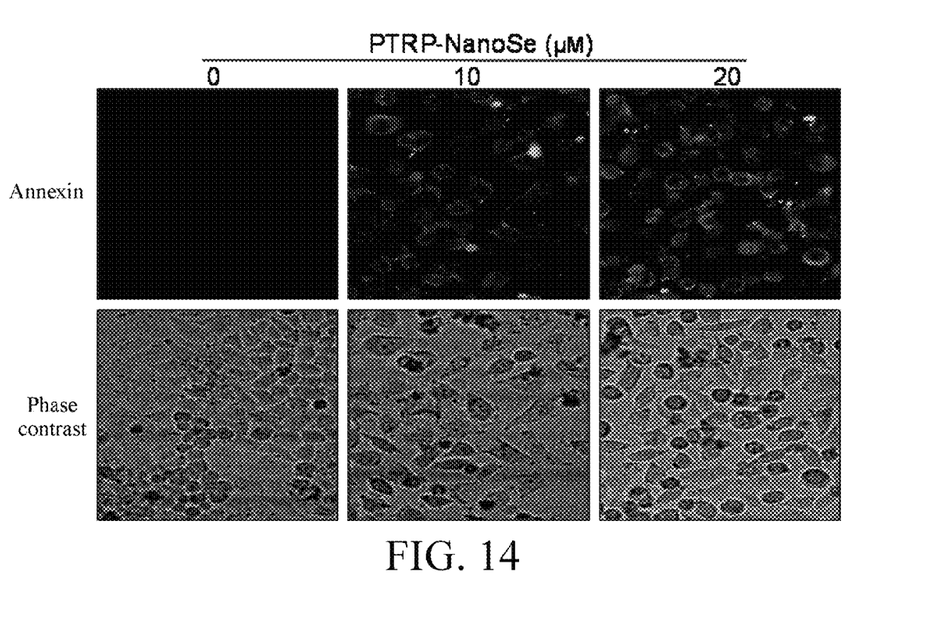
FIG. 14 shows externalization of phosphatidylserine detected by the Annexin-V method when *Pleurotus tuber-regium* polysaccharide functionalized nano-selenium is used to induce apoptosis of human breast cancer cell line MCF-7.

FIG. 14 shows externalization of phosphatidylserine detected by the Annexin-V method (Bio-Radiance 2100MP Scanning System equipped with 488 nm argon laser) when *Pleurotus tuber-regium* polysaccharide functionalized nano-selenium is used to induce apoptosis of human breast cancer cell line MCF-7, and the results show that functionalized nano-selenium can cause externalization of phosphatidylserine of the cell line MCF-7, and with the increase of the concentration of functionalized nano-selenium, the externalization of phosphatidylserine is more obvious, that is, the proportion of apoptotic cells is large in the early stage.

In view of the test results, water-soluble *Pleurotus tuber-regium* polysaccharide functionalized nano-selenium can induce apoptosis of human breast cancer cell line MCF-7, that is, water-soluble *Pleurotus tuber-regium* polysaccharide functionalized nano-selenium has effective function of inhibiting proliferation of human breast cancer cells, and with the increase of the concentration of functionalized nano-selenium, the proportion of apoptotic cells is increased due to the dose-dependent response.

As will be understood and appreciated by those skilled, in methods for preparing nano-elemental selenium in the prior art, the morphology is modified or regulated by using various different modifiers or regulating agents to obtain a product with desired particle size and morphology. As will also be appreciated by those skilled in the art, however, the modifiers are not biomolecules with high biological activity, such that the biological activity of nano-elemental selenium, especially the anti-tumor activity, cannot be effectively enhanced by the modifier or regulating agent, that is, the resulting product is not functionalized nano-elemental selenium, in contrast to the present invention.

The present invention has been disclosed above through specific embodiments, but persons of ordinary skill in the art should understand that various variations and equivalent replacements may be made without departing from the scope of the present invention. Additionally, in order to be adapted to specific situations or materials in the technology of the present invention, various modifications may be made without departing from the protection scope of the present invention.

What is claimed is:

1. A *Pleurotus tuber-regium* polysaccharide functionalized nano-selenium hydrosol with anti-tumor activity, comprising:
   *Pleurotus tuber-regium* polysaccharides, in a concentration range of 10 mg·L$^{-1}$-1000 mg·L$^{-1}$;
   Vitamin C, in a concentration range of 0.02 mmol·L$^{-1}$-20 mmol·L$^{-1}$; and nano-selenium, in a concentration range of 0.005 mmol·L$^{-1}$-5 mmol·L$^{-1}$;
   wherein the *Pleurotus tuber-regium* polysaccharide functionalized nano-selenium hydrosol is prepared by steps of:
       Step 1) at a temperature in a range of 15-35° C., adding a Vitamin C solution to an aqueous solution of *Pleurotus tuber-regium* polysaccharides, and mixing uniformly;
       Step 2) adding dropwise a selenium dioxide solution or a selenite solution to the solution obtained in Step 1 while mixing uniformly; and
       Step 3) adding water to the solution obtained in Step 2 to a pre-determined volume, to obtain a *Pleurotus tuber-regium* polysaccharide functionalized nano-selenium hydrosol when the red color of the product is no longer deepened.

2. An anti-tumor drug comprising the *Pleurotus tuber-regium* polysaccharide functionalized nano-selenium hydrosol with anti-tumor activity according to claim 1.

3. A *Pleurotus tuber-regium* polysaccharide functionalized nano-selenium hydrosol with anti-tumor activity, comprising:

*Pleurotus tuber-regium* polysaccharides, in a concentration range of 10 mg·L$^{-1}$-1000 mg·L$^{-1}$;

Vitamin C, in a concentration range of 0.02 mmol·L$^{-1}$-20 mmol·L$^{-1}$; and nano-selenium, in a concentration range of 0.005 mmol·L$^{-1}$-5 mmol·L$^{-1}$, wherein an average particle size of the *Pleurotus tuber-regium* polysaccharide functionalized nano-selenium hydrosol is about 95 nm.

4. A *Pleurotus tuber-regium* polysaccharide functionalized nano-selenium hydrosol with anti-tumor activity, comprising:

*Pleurotus tuber-regium* polysaccharides, in a concentration range of 10 mg·L$^{-1}$-800 mg·L$^{-1}$;

Vitamin C, in a concentration range of 2 μmol·L$^{-1}$-0.01 mmol·L$^{-1}$; and nano-selenium, in a concentration range of 0.1 mmol·L$^{-1}$-5 mmol·L$^{-1}$.

5. The *Pleurotus tuber-regium* polysaccharide functionalized nano-selenium hydrosol with anti-tumor activity according to claim 4, wherein the *Pleurotus tuber-regium* polysaccharide functionalized nano-selenium hydrosol is prepared by steps of:

Step 1) at a temperature in a range of 15-35° C., adding a Vitamin C solution to an aqueous solution of *Pleurotus tuber-regium* polysaccharides, and mixing uniformly;

Step 2) adding dropwise a selenium dioxide solution or a selenite solution to the solution obtained in Step 1 while mixing uniformly; and Step 3) adding water to the solution obtained in Step 2 to a pre-determined volume, to obtain a *Pleurotus tuber-regium* polysaccharide functionalized nano-selenium hydrosol when the red color of the product is no longer deepened.

6. The *Pleurotus tuber-regium* polysaccharide functionalized nano-selenium hydrosol with anti-tumor activity according to claim 4, wherein an average particle size of the *Pleurotus tuber-regium* polysaccharide functionalized nano-selenium hydrosol is about 95 nm.

7. A method for preparing the *Pleurotus tuber-regium* polysaccharide functionalized nano-selenium hydrosol with anti-tumor activity according to claim 1, comprising steps of:

Step 1) at a temperature in a range of 15-35° C., adding a Vitamin C solution to an aqueous solution of *Pleurotus tuber-regium* polysaccharides, and mixing uniformly;

Step 2) adding dropwise a selenium dioxide solution or a selenite solution to the solution obtained in Step 1 while mixing uniformly; and Step 3) adding water to the solution obtained in Step 2 to a pre-determined volume, to obtain a *Pleurotus tuber-regium* polysaccharide functionalized nano-selenium hydrosol when the red color of the product is no longer deepened.

8. The method for preparing the *Pleurotus tuber-regium* polysaccharide functionalized nano-selenium hydrosol with anti-tumor activity according to claim 7, wherein the concentration of the aqueous solution of *Pleurotus tuber-regium* polysaccharides is 30 mg·L$^{-1}$-3000 mg·L$^{-1}$, the concentration of the Vitamin C solution is 0.2 mmol·L$^{-1}$-200 mmol·L$^{-1}$, and the concentration of the selenium dioxide solution or the sodium selenite solution is 0.05 mmol·L$^{-1}$–50 mmol·L$^{-1}$.

9. The method for preparing the *Pleurotus tuber-regium* polysaccharide functionalized nano-selenium hydrosol with anti-tumor activity according to claim 7, wherein the concentration of the aqueous solution of *Pleurotus tuber-regium* polysaccharides is 100 mg·L$^{-1}$–3000 mg·L$^{-1}$, the concentration of the Vitamin C solution is 0.02 mol·L$^{-1}$-0.2 mol·L$^{-1}$, and the concentration of the selenium dioxide solution or the sodium selenite solution is $1\times10^{-6}$ mol·L$^{-1}$-$1\times10^{-2}$ mmol·L$^{-1}$.

10. The method for preparing the *Pleurotus tuber-regium* polysaccharide functionalized nano-selenium hydrosol with anti-tumor activity according to claim 7, wherein Vitamin C is reductive Vitamin C.

11. The method for preparing the *Pleurotus tuber-regium* polysaccharide functionalized nano-selenium hydrosol with anti-tumor activity according to claim 7, wherein the selenite is sodium selenite.

12. The method for preparing the *Pleurotus tuber-regium* polysaccharide functionalized nano-selenium hydrosol with anti-tumor activity according to claim 7, wherein the *Pleurotus tuber-regium* polysaccharides are water-soluble *Pleurotus tuber-regium* polysaccharides, chemically modified hot alkali-soluble *Pleurotus tuber-regium* polysaccharides, or a combination thereof.

13. A method for storing the *Pleurotus tuber-regium* polysaccharide functionalized nano-selenium hydrosol with anti-tumor activity according to claim 1, wherein the *Pleurotus tuber-regium* polysaccharide functionalized nano-selenium hydrosol is stored in the form of a sol at 2-10° C.

\* \* \* \* \*